United States Patent
Claessens (10) Patent No.: US 6,551,286 B1
(45) Date of Patent: Apr. 22, 2003

(54) SAFETY CAP FOR A CANNULA (76) Inventor: Albert Louis Victor Jozef Claessens, Guldensporenlaan 70b, B-3530 Houthalen (BE)

( * ) Notice: Subject to any disclaimer, the term of this patent is extended or adjusted under 35 U.S.C. 154(b) by 35 days.

(21) Appl. No.: 09/699,719

(22) Filed: Oct. 30, 2000

(30) Foreign Application Priority Data

Nov. 11, 1999 (DE) .......................................... 199 54 373

(51) Int. Cl.$^7$ ................................................ A61M 5/00
(52) U.S. Cl. ..................... 604/263; 604/192; 604/198; 604/187; 128/919
(58) Field of Search ................................ 604/192, 198, 604/187, 263, 197, 110, 195; 128/919; 206/365, 366

(56) References Cited

U.S. PATENT DOCUMENTS

| 3,865,236 A | | 2/1975 | Rycroft |
| 4,169,123 A | * | 9/1979 | Moore et al. ............... 222/519 |
| 4,735,311 A | | 4/1988 | Lowe |
| 4,775,367 A | | 10/1988 | Schmidt |
| 4,986,818 A | * | 1/1991 | Imbert et al. ............... 604/192 |
| 5,098,400 A | | 3/1992 | Crouse et al. |
| 5,147,325 A | | 9/1992 | Mitchell et al. |

FOREIGN PATENT DOCUMENTS

| DE | 8906101/2 | | 6/1989 |
| DE | 4234319 A1 | | 10/1992 |
| EP | 079498 B1 | | 2/1968 |
| EP | 0716860 A2 | | 12/1995 |
| EP | 0 903 157 A2 | | 9/1998 |
| WO | WO 94/13336 | * | 6/1994 |

* cited by examiner

*Primary Examiner*—Michael J. Hayes
*Assistant Examiner*—Kathryn L. Thompson (57) ABSTRACT

Safety cap for a cannula, comprising an outer sleeve (10) having a rolling end (11) and a top end (12) made of a rigid plastic material and a seal element (30) made of a gas-permeable, flexible plastic held inside the outer sleeve (10), having a channel (33) closed at one end to seal off the opening at the tip of the cannula, characterized in that the outer sleeve (10) is interrupted by at least one lateral opening (18) in its long side between the bottom end (11) and the top end (15).

10 Claims, 10 Drawing Sheets

SAFETY CAP FOR A CANNULA

FIELD OF THE INVENTION

The present invention relates to improvements in safety caps for a cannula. The invention pertains to a safety cap for a cannula, consisting of an outer sleeve of a rigid plastic component and a seal element of a gas permeable, flexible plastic component, held in the outer sleeve. The seal element is provided with a channel, closed at one end, for sealing the opening at the tip of the cannula.

BACKGROUND OF THE INVENTION

Safety caps of this type are used in the medical field and have already been known for a long time for cannulas and for syringes equipped with cannulas. Their purpose is to make it possible for the cannulas to be packaged under sterile conditions without damage to the packaging material and to reduce the risk of injury during handling. In addition, the safety caps serve to prevent damage to the thin, bevel-ground tips of the cannulas. On occasion, the safety caps are also replaced on the cannulas after use.

Before they are used, the safety caps from production must first be sterilized. The cannulas and the syringes must also be sterilized. This is done with gaseous media such as steam or ethylene oxide gas (ETO). The items mentioned are usually used only once and then discarded in order to prevent the transfer of disease. In view of the large quantitative demand for these items, therefore, it is very important that it be possible to produce them easily and rapidly. The way in which these items are designed, however, must always take into account the goal of minimizing the risk of injury and infection.

SUMMARY OF THE INVENTION

According to the invention, a safety cap for a cannula which has an outer sleeve of a rigid plastic component and a seal element of a flexible plastic component held in the outer sleeve to seal off the opening at the tip of the cannula is described in DE 4,234,319 A1. This cap is produced by a two-component injection-molding process. The known safety cap, however, is still in need of improvement with respect to sterilization and handling.

The known safety cap for cannulas is sterilized before use. Because the rigid plastic component of the outer sleeve is impermeable to gas, however, the gaseous sterilizing medium can reach the interior areas only with difficulty. These caps must therefore be held for a long time in the sterilizer to ensure that all the germs and pathogens are killed. In this respect, sterilization in the ready-to-be-packaged state with the cap set in place on the cannula is even less favorable. Because the goal has always been to meet the highest sterility standards, so far little or no attention has been given to reducing the time it takes to sterilize the caps.

The outer sleeve made of rigid plastic gives the known safety cap sufficient rigidity toward the outside, whereas the seal element of flexible plastic seals the opening at the tip of the cannula. To minimize the risk of injury and infection, the outer sleeve extends continuously and without a break over the entire length of the exposed area of the cannula to be protected. The safety cap is connected to the syringe exclusively by the flexible component, and at the insertion opening the safety cap consists entirely of this flexible component. Nevertheless, the flexible design of the insertion opening of the safety cap has certain disadvantages with respect to the reliability with which the cap can be gripped when the cannula is being reinserted into the cap, because the cap can easily be squeezed in too much.

The invention is therefore based on the task of creating a safety cap for a cannula which can be produced efficiently and handled safely and which is characterized by excellent sterilization behavior.

This task is accomplished by a safety cap of the general type described above in which the outer sleeve is interrupted by at least one lateral opening on the long side between its bottom end and its top end.

As a result, it become possible to sterilize the safety cap effectively and quickly even after it has been placed on the cannula. The route taken by the gaseous sterilization medium into the interior of the safety cap is considerably reduced by the openings provided in the side of the outer wall of the cap. Furthermore, in cases where both parts are sterilized simultaneously with the safety cap in place on the cannula, there is no longer any need for the insertion opening of the safety cap to be made of flexible plastic to allow the entry of the gas. This also leads to the possibility of a design which offers improved handling.

In accordance with an advantageous design, the bottom end of the outer sleeve has an essentially cylindrical base section, possibly tapering slightly toward the top end, with an insertion opening for the cannula profiled tope section is disposed adjacent to the base. Parts of the profiled top section following in the longitudinal direction of the safety cap have a cross section which is not round on the outside. This top section extends all the way to the top end of the outer sleeve. The safety cap is thus reliably prevented from rolling away when it is not attached to the cannula, which improves the handling aspect. That the safety cap for the cannula can be counted on to stay put also helps indirectly to reduce the spread of infection, because the possibility is reduced that the cap could fall to the floor, be picked up, and be put back on the cannula, a situation which could allow the syringe to be used again in error.

In accordance with another advantageous of the invention, the outer sleeve has a pass-through opening for insertion feature, the seal element and which is sealed off at the top end of the outer sleeve by the seal element. Each of the lateral openings is located in a section of the outer wall of the outer sleeve which has been recessed in the direction of the pass-through opening through the outer sleeve. Thus, the lateral openings lie outside the direct gripping area of the outer wall. It is known that cannulas are beveled off at the free end, so that the end of the cannula has a taper in contrast to the main tubular section itself. The end of the cannula can therefore penetrate relatively easily into a plastic body or even pass through it completely if the plastic is thin-walled. The tubular section, however, offers greater resistance to complete insertion or penetration. As a result of the design measures described above, the danger of injury, especially in the area of the lateral openings of the outer sleeve, is avoided in the event that the safety cap is mistakenly pushed slantwise onto the cannula. Accordingly, even if the tip of the cannula passes through the outer sleeve, it cannot extend far enough to reach the fingers of the person handling the cannula. The depth of the recessed area will thus preferably be calculated in such a way that the tip of the cannula will still be within the recess at the time the tubular section with its larger cross section reaches the sleeve and the resistance to penetration thus starts to increase significantly.

To simplify production in an injection-molding process, it is advantageous for the recessed section to extend in the longitudinal direction of the outer sleeve, so that no undercuts are formed.

It has been found that providing lateral openings large enough for sterilization does not significantly increase the risk of penetration of the outer wall by the needle. In a further elaboration of the invention, an especially reliable solution is obtained by providing the edge of the lateral opening which is at the top in terms of the insertion direction of the cannula with an outward-projecting safety tongue, the inside wall section of which slants inward toward the top end of the outer sleeve. If for some reason the safety cap is pushed onto the cannula at an extreme slant, the cannula will strike this wall section of the tongue, which more effectively prevents the outer sleeve from being penetrated. The slant of the tongue deflects the cannula, which has been inserted at a slant, back into the correct position. In addition, the outward-bent form of the protective tongue makes it possible to enlarge the lateral opening without any loss of safety. Accordingly, a large entry region for the sterilizing medium can be created, which brings about a further improvement in the sterilization behavior.

In accordance with another advantageous embodiment of the invention, the top section has an essentially cylindrical base element, possibly tapering slightly toward the top; this base element is provided with four ribs, each of which begins at the base and extends in the longitudinal direction of the safety cap. This design combines ease of production by injection molding with the ability to prevent the cap from rolling away in the loose state; at the same time, the ribs also provide high structural rigidity.

A shape which is especially easy to grip is obtained when each of the ribs is oriented at a slant with respect to the radial direction of the outer sleeve in such a way that the top section acquires a cross section in the form of an "H". In this case the wide, flattened outer flanks of the H offer a relatively large contact surface for the fingers of the person handling the cap, who can thus grip the cap securely and guide it to the cannula with the correct orientation.

It is preferable here for each of the lateral openings to be located in a section of the wall between two essentially parallel ribs. As a result, a shape is obtained which has high safety potential with respect to the risk of injury, because the recessed area offers a high degree of protection in the event that the cannula penetrates the safety cap in the weakest area of the outer wall, namely, the lateral openings in the outer sleeve.

The lateral openings are preferably directly adjacent to the base section, that is, to the area which tends to have the greatest wall thickness, so that the weakening of the rigidity of the outer wall associated with the lateral openings is minimized. In addition, the lateral openings thus become located approximately in the middle of the cap, seen in its longitudinal direction, so that the route taken by the sterilization medium into the cap remains short, as a result of which the sterilization behavior is further improved.

In yet another advantageous embodiment of the invention, the lateral openings in the outer sleeve are covered on the inside by the seal element. Thus, the safety cap acquires a closed external form with respect to the cannula, so that, after the syringe has been filled and a sterile cannula with its safety cap has been set in place, any danger of contamination to the cannula is excluded, especially in cases where the content of the syringe is not injected immediately thereafter.

So that the seal element will be held securely in the outer sleeve, the top section is provided in an advantageous embodiment along its inside wall in the area of each of the lateral openings with a groove extending in the longitudinal direction of the outer sleeve. These grooves are open at the end facing the base, and the seal element is provided with radial projections which fit into the grooves and preferably fill them completely.

In accordance with another advantageous design, the bottom end of the outer sleeve is designed as a collar, which surrounds the insertion opening and extends essentially in the radial direction. This serves as to protect the fingers when the cap is being replaced on the cannula and can also serve as a stop, which strikes a cone provided on the cannula or on the end of the syringe and thus prevents the cap from being pushed on too far and top end from being penetrated. As a result, the overall length of the cap can be reduced, which has the effect of conserving material without impairing its safety function.

The collar is preferably designed as a cone pointing toward the top end, so that, if the person handling the cannula misses the insertion opening and the tip of the cannula thus strikes the collar, the tip is prevented from slipping off toward the finger holding the cap. Instead, the slightly conical shape has the effect of redirecting the path of the cannula toward the insertion opening.

Yet another advantageous design makes it easier to set the safety cap down onto the cannula, in that the closed channel of the seal element is designed with a continuous taper at the beginning, pointing toward the closed end; this tapered part is then followed by an end section, into which the opening at the top of the cannula penetrates in the fully inserted state, the inside diameter of this end section being smaller than outside diameter of the tubular section of the cannula. As a result, the cannula can first be introduced freely into the bottom end of the cap, where the tapered section of the channel in the seal element is able to correct the direction in which the cannula is being inserted, if necessary. Then, toward the end of the insertion movement, the opening of the cannula becomes tightly enclosed by the seal element. Thus the desired seal effect is obtained in addition to elastic support for the top end of the cannula, which is protected from damage as a result.

In yet another advantageous design of the invention, the handling of the safety cap is improved even more by providing the section at the top of the longitudinal axis of the cap with two opposing narrow sides and two opposing wide sides, each of the latter being designed as gripping surfaces provided with anti-slip projections and/or depressions and/or holes.

The top section, furthermore, can be designed with a cylindrical base body which tapers conically toward the top end with ribs extending in the longitudinal direction of the safety cap. This conically tapering base body has several lateral openings between each pair of adjacent ribs, these openings being designed as elongated slots oriented crosswise to the longitudinal direction of the safety cap. The slots are filled with the material of the flexible plastic component. With this advantageous design, an excellent sterilization behavior is obtained, because the penetration routes of the sterilizing medium can be kept very short. The slot-like shape of the lateral openings offers only very small surface areas vulnerable to attack by the tip of cannula and thus minimizes the chance that the cannula could unintentionally penetrate the outer wall of the safety cap, but at the same time this shape guarantees optimum accessibility to the sterilizing medium. Because the slots are filled with the flexible component, an almost completely smooth outward appearance is obtained. This means that is impossible for any random objects that may be lying about to hook onto the slots and unintentionally pull the cap off the cannula. If the filler material is provided with a nubbly, outward-curved surface, it is also possible, if desired, to create slip-proof gripping areas.

So that the cannula safety cap can be produced efficiently, it is preferable to design it as a two-component, injection-molded part.

BRIEF DESCRIPTION OF THE DRAWINGS

These and other objects of the present invention and various features and details of the operation and construction thereof are hereinafter more fully set forth with reference to the accompanying drawings, wherein.

DETAILED DESCRIPTION OF THE PREFERRED EMBODIMENT

As can be seen from the drawing, the cannula safety cap according to the first exemplary embodiment, which is illustrated in FIGS. 1–10, is formed by an outer sleeve 10 and a seal element 30, which is held inside the outer sleeve. The outer sleeve 10 gives the safety cap a rigidity which is sufficient for the cap to be gripped. In addition, the sleeve is made strong enough to resist puncture by the tip of a cannula K or an injection needle. The seal element 30, in contrast, serves primarily to seal off the opening at the tip of the cannula and to provide protective, elastic support for the tip. The safety cap is thus especially suitable for being packaged together with syringes of the type which are sold already assembled, filled, and ready to use.

The outer sleeve 10 of the safety cap consists of a rigid plastic component, whereas the seal element 30 is made of a gas-permeable, flexible plastic component. Both are produced together in a two-component, injection-molding process. The outer sleeve 10 is preferably molded first, and then the seal element 30 of flexible plastic is molded onto it, so that the two parts are bonded together by adhesion.

It is also possible, however, to mold the outer part 10 first in a first mold, to introduce it into a second injection mold, and to inject the flexible component in it there. The elements can also be produced separately and simply assembled.

The outer sleeve 10 has a base section 13, the wider, bottom end 11 of which has essentially the form of a circular cylinder on the outside; this forms the opening 12 into which the cannula K can be inserted in the longitudinal direction. So that it can be produced more easily, this base section tapers down slightly toward the top end 15 of the safety cap. Adjoining the base section 13 in the insertion direction of the cannula is a top section 14, which extends all the way to the top end 15 of the outer sleeve 10. The outer sleeve 10 itself is designed as a hollow body with a central pass-through opening 16.

The outer sleeve 10, furthermore, is provided along its longitudinal outside wall with at least one lateral opening; in the present case, it is provided with two opposing lateral openings 18, which are immediately adjacent to the base section 13. In the first exemplary embodiment, the lateral openings 18 are located approximately in the middle, seen in the longitudinal direction, of the cannula safety cap. It is advisable to locate them in such a way that the routes to be taken by the gaseous sterilization medium such as steam or ethylene oxide gas will be short.

The top section 14, the cross section of which is not round, has an essentially cylindrical base body 20, which, in the exemplary embodiment, tapers down slightly toward the top end 15 to facilitate production by injection molding. The wall thickness of the base body 20 is essentially uniform.

Four ribs 21, furthermore, which begin directly at the base section 13, are also provided on the top section 14 to prevent a loose safety cap from rolling away. These ribs 21 are connected to the outside surface of the base body 20 and extend in the longitudinal direction of the safety cap. Each of the ribs 21 is arranged at a slant to the radial direction of the outer sleeve in such a way that the top section 14 has a cross section in the form of an "H". In the area of the outside flanks of the H, which form an approximately flat surface, the top section 14 thus has two wide, opposing gripping areas 22, which are connected to each other by the recessed sections 17 of the H, which are comparatively narrow.

The previously mentioned lateral openings 18 are located in the recessed walls sections 17 between two essentially parallel ribs 21, so that even if the tip of a cannula should project slightly to the outside through one of the lateral opening 18, the danger of injury to the person handling the cannula is avoided.

Figure 13:
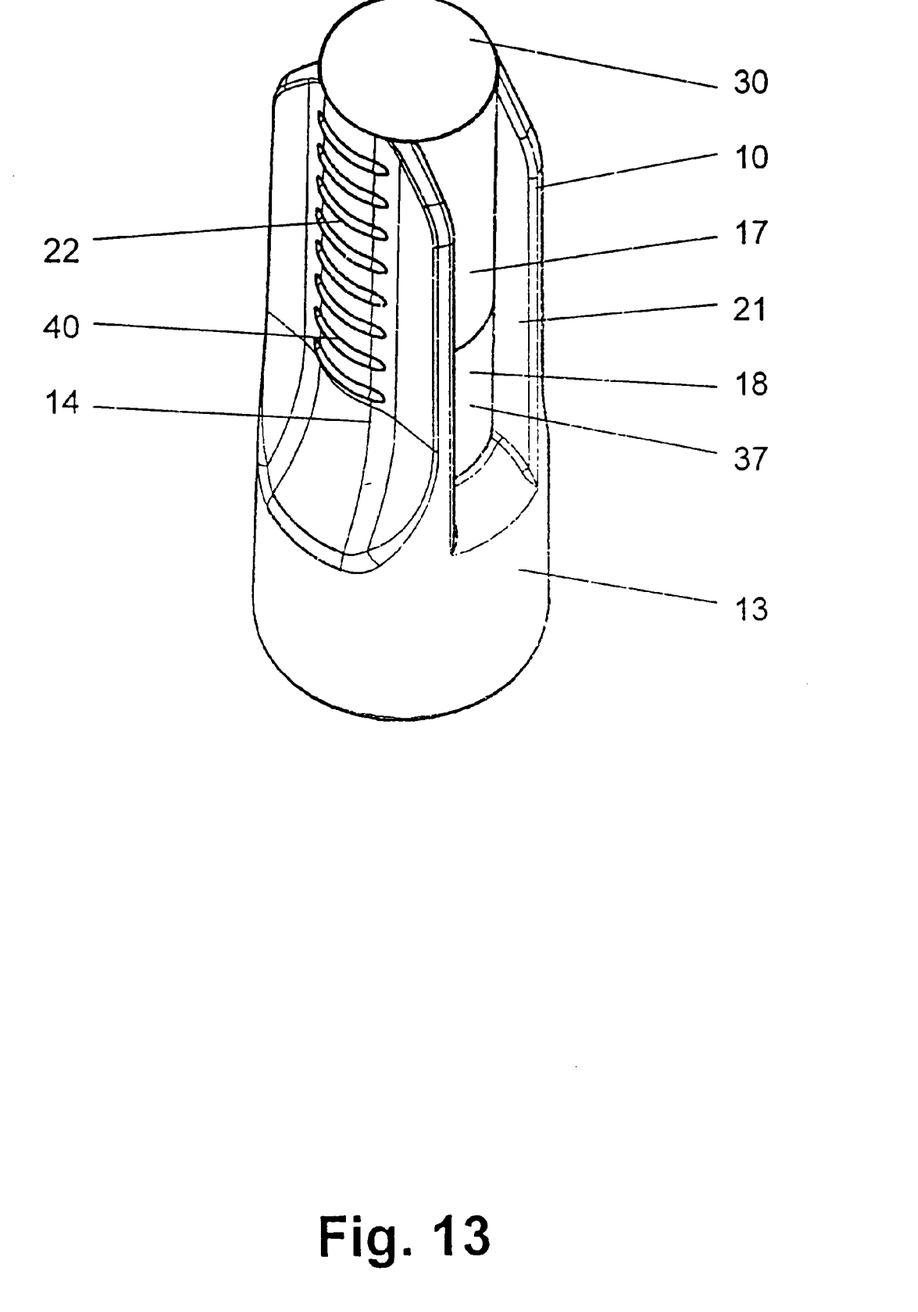
FIG. 13 shows a perspective view of a third exemplary embodiment of a safety cap, which is provided with transverse ribs along its gripping surfaces.

In an alternative design, not shown in the drawing, each of the lateral openings 18 is formed by several slots extending transversely to the longitudinal direction, these slots being arranged in rows in the longitudinal direction, like the anti-slip projections or recesses 40 shown in FIG. 13. The slots are located essentially in the area of the openings 18 shown in FIGS. 1–10. This slot design has the effect of providing even greater protection against the protrusion of the cannula to the outside in this area.

As can also be derived in particular from FIGS. 4–10, the seal element 30 is seated inside the outer sleeve 10. Only a mushroom-like top end section 31 projects slightly through an axial opening 19 at the top end 15 of the outer sleeve 10 in order to close off the cannula safety cap with a flexible, slightly curved tip.

Behind the top end section 31 of the seal element 30, the latter has a seal plug section 32, in which, on the inside, a receiving channel 33 for the cannula K is provided, this channel being closed at one end. The closed channel 33 of the seal element 30 is provided first with a section 34, which tapers continuously toward the closed end. The cross section of this part begins as a multiple of the diameter of the tubular section of a cannula K. The section 34 of the channel 33 is followed by an end section 35, into which the opening at the tip of the cannula penetrates when fully inserted. The inside diameter of the end section 35 is smaller than the outside diameter of the top section of the cannula, which means that the elastic material of the seal element is slightly deformed. As a result of this deformation of the tip-receiving channel 33, which is designed as a blind hole and which is located on the longitudinal axis of the cannula safety cap, the insertion resistance and also the flexural forces possibly acting on an imprecisely guided cannula tip remain minimal.

Figure 8:
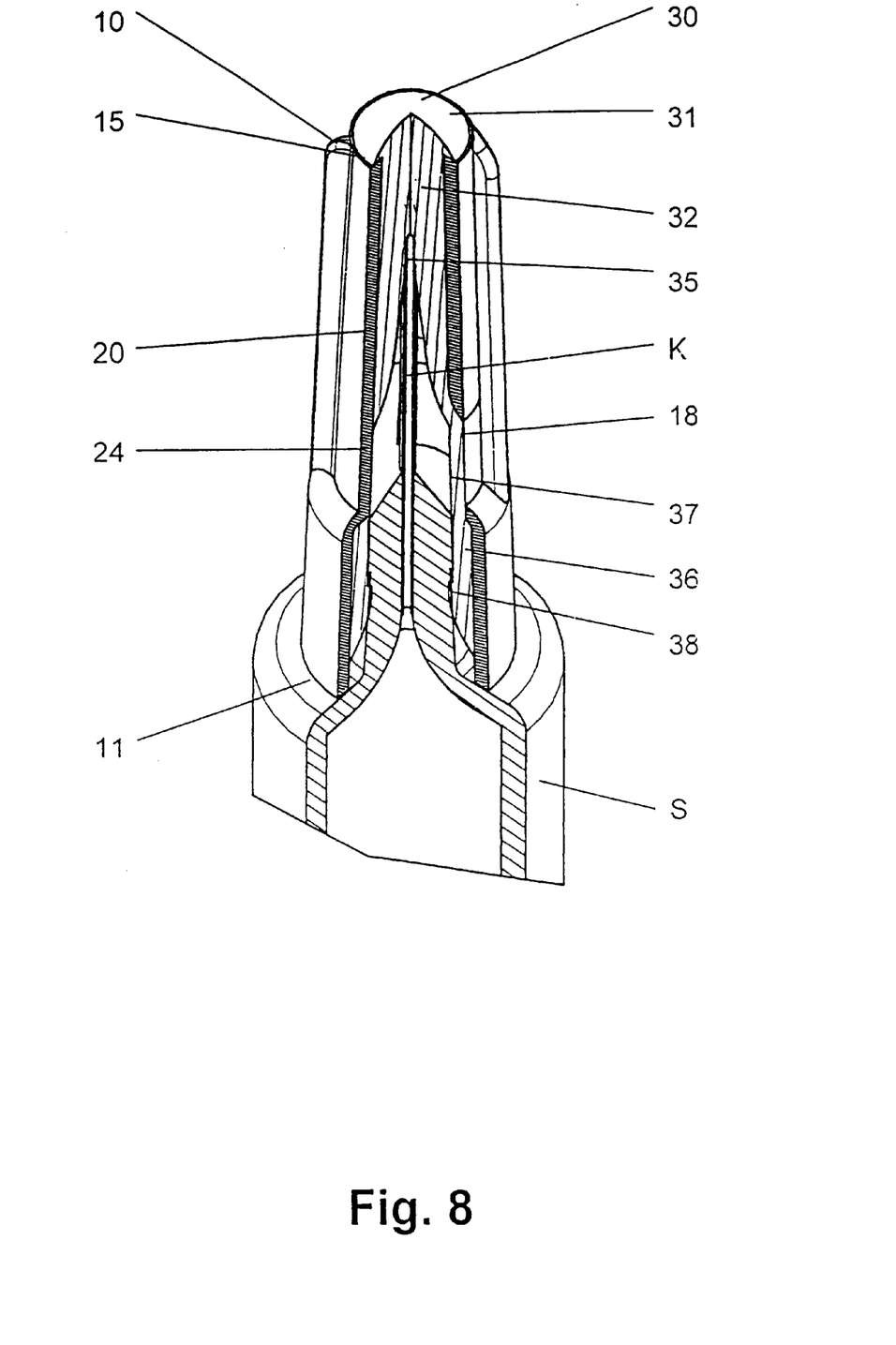
FIG. 8 shows a view corresponding to FIG. 5 for the purpose of illustrating the relative positions of the safety cap and a syringe with integrated cannula.

As can be derived from FIG. 8, a section 36, which is slightly conical on the inside, adjoins the seal plug section 32 in the direction toward the insertion opening 12; the cone of a cannula or the base of a syringe S can be brought to rest against this conical section upon insertion. Although one conical section 36 can be used with different types of cannulas or syringes, it is recommended that it be adapted to the specific shape of the selected cannula or syringe.

The slightly conical section 36 also covers up the lateral openings 18 in the outer sleeve 10. In addition, the top section 14 is provided on its inside wall with grooves 23 in the area of the lateral openings 18; these grooves extend in the longitudinal direction of the outer sleeve 10 and are open at the end facing the base. As can be derived from FIGS. 9 and 10, the seal element 30 has radial projections 37 on the outside surface of the slightly conical section 36; these projections fit into the grooves 23 and preferably fill them completely.

From the seal plug section 32 toward the insertion opening 12, the seal element 30 extends with relatively thin walls along the inside of the top section 14 and then of the base section 13 of the outer sleeve 10. As can be seen from FIGS. 9 and 10, the seal element 30 does not completely cover the inside wall of the outer sleeve 10. Instead, sections 24 of the inside wall of outer sleeve 10 remain uncovered in the area of the slightly conical section 36 at the level of the lateral openings 18. Nevertheless, the seal element 30, as previously mentioned, extends over the lateral openings 18 in order to protect the cannula K from contamination by the intrusion of foreign particles from the outside.

Figure 9:
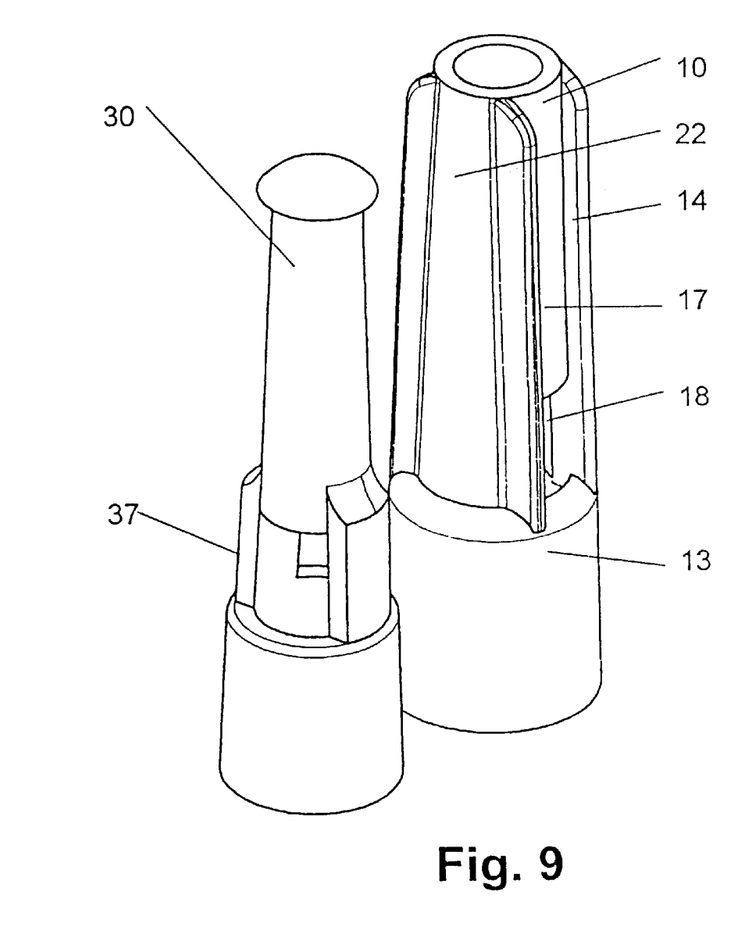
FIG. 9 shows a perspective view of an outer sleeve and a seal element of a safety cap, which are presented here next to each other for the sake of illustration.
Figure 10:
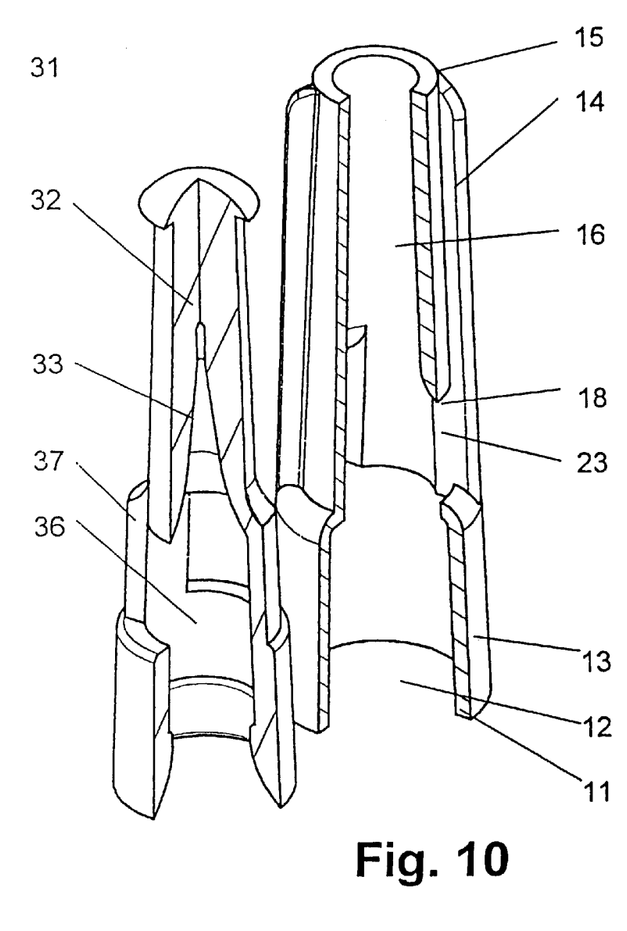
FIG. 10 shows a perspective view according to FIG. 9 but with a partially cut-away outer sleeve and a partially cut-away seal element.

The bottom end of the seal element 30 is formed by a seal projection with a seal lip 38, which reduces the free inside diameter of the safety cap. The bottom end 39 of the seal element thus expands inward to form the lip.

Figure 1:
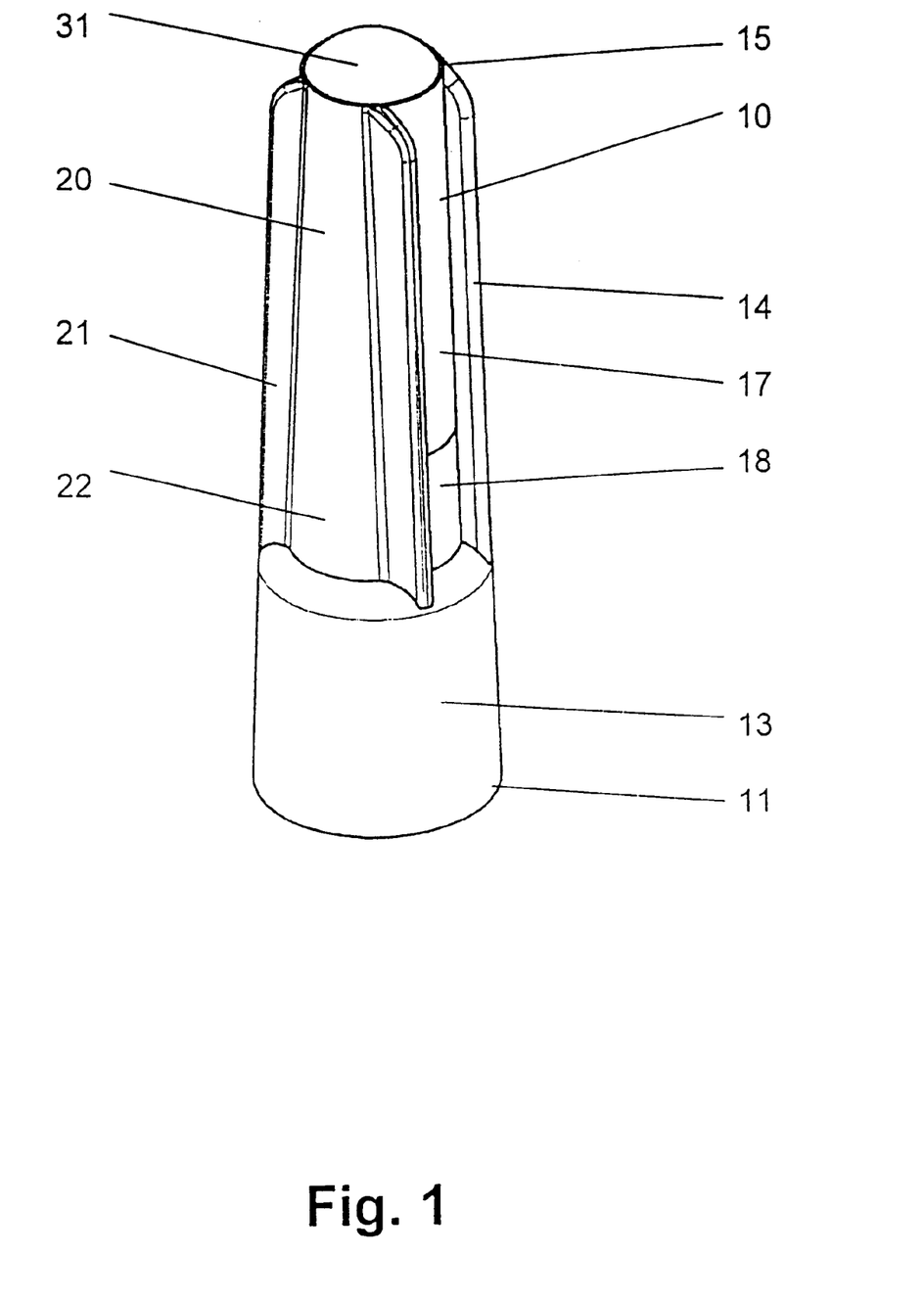
FIG. 1 shows a perspective view of a first exemplary embodiment of a safety cap for a cannula.
Figure 2:
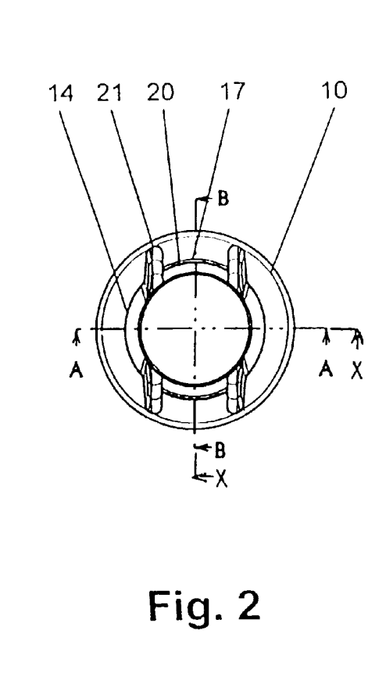
FIG. 2 shows a view from above onto the safety cap of FIG. 1.
Figures 3, 4:
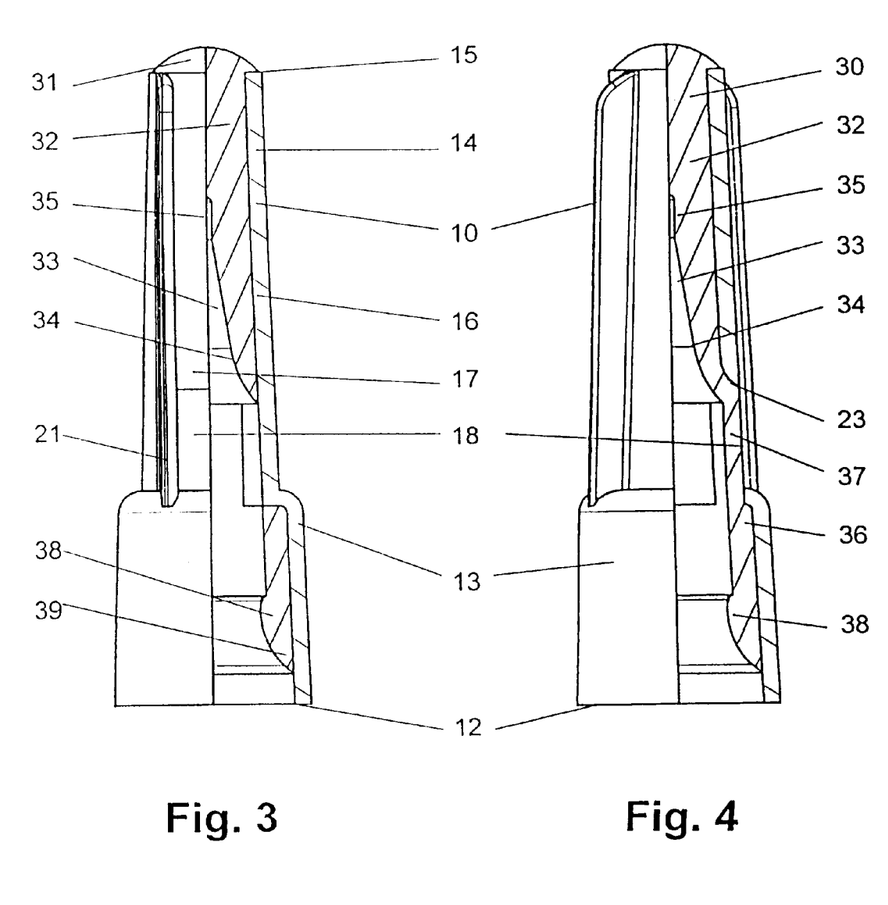
FIG. 3 shows a side view of the safety cap of FIG. 1, where the right half is shown as a cross section along line A—A of FIG. 2.
FIG. 4 shows a side view of the safety cap of FIG. 1, which has been rotated 90ø with respect to the view of FIG. 3, the right half representing a cross section along line B—B of FIG. 2.
Figure 5:
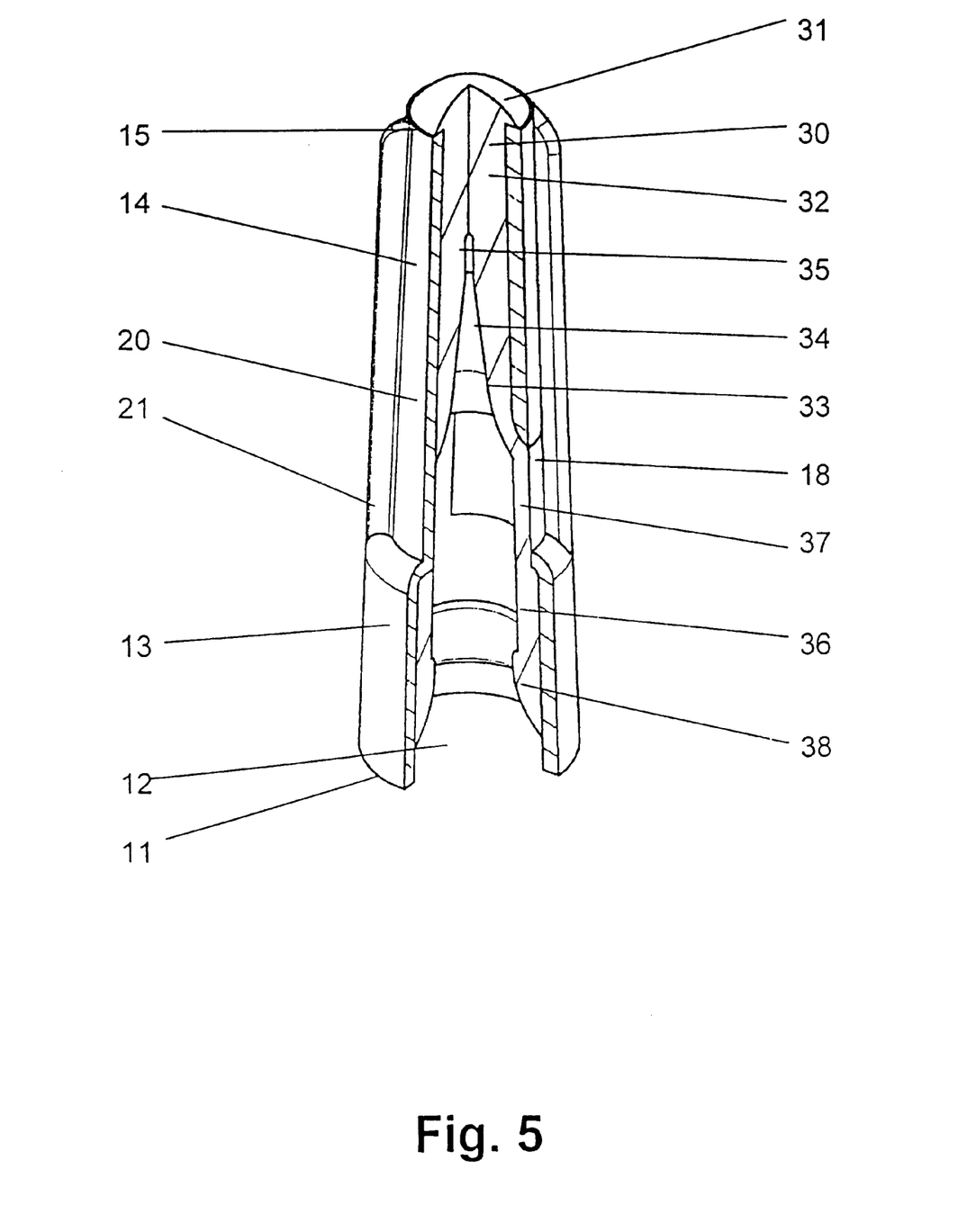
FIG. 5 shows another perspective view of the first exemplary embodiment, in which a quarter-segment corresponding to line X—X in FIG. 2 has been cut away.
Figure 6:
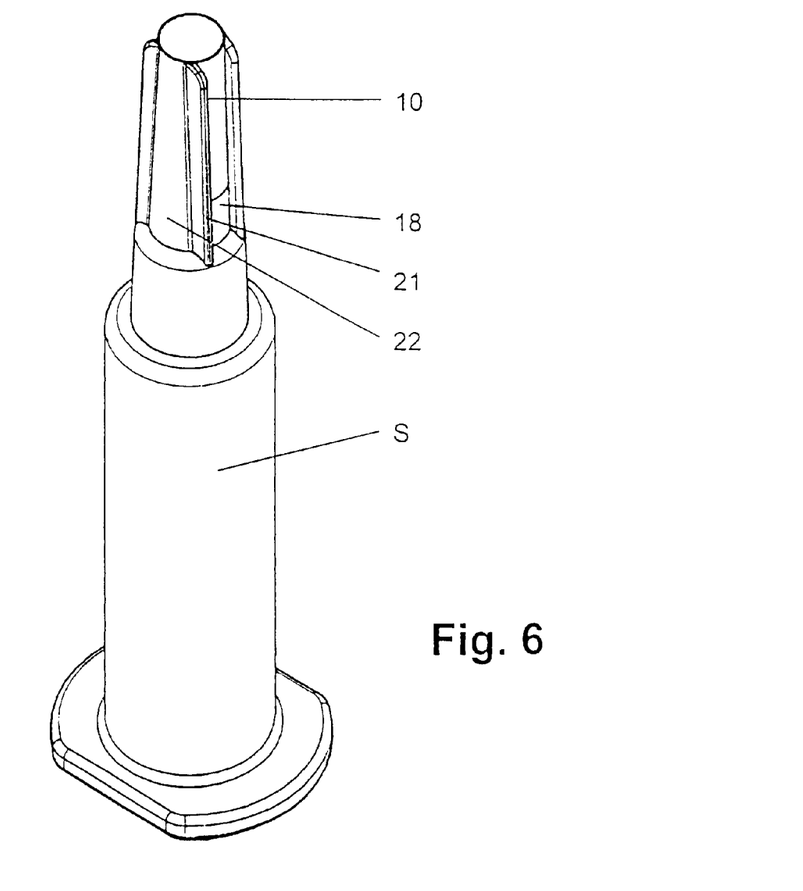
FIG. 6 shows a perspective view of the safety cap according to the first exemplary embodiment after the cap has been placed onto a syringe.
Figure 7:
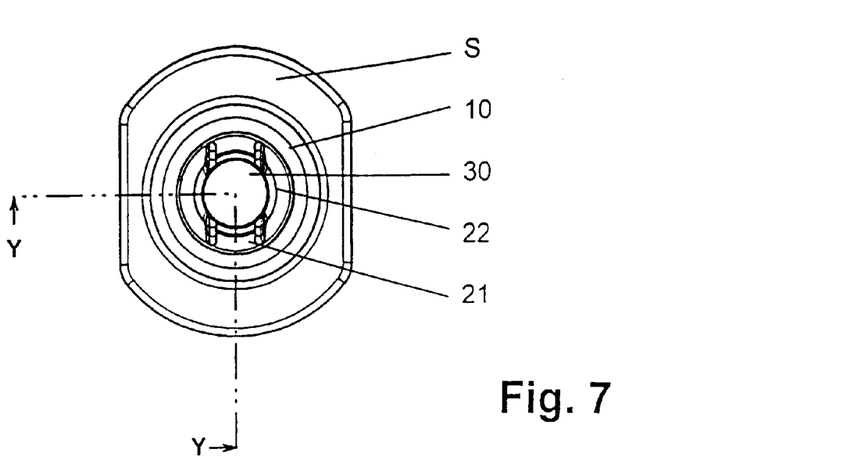
FIG. 7 shows a view from above onto the design of FIG. 6.

The bottom end of the cannula safety cap is formed by the outer sleeve 10, which is made of the rigid plastic component, so that a sure-grip edge is obtained at the bottom end of the cap. At the same time, the bottom edge of the outer sleeve 10 forms a stop, which prevents the safety cap from being pushed too far onto the cannula K. In the completely pushed-on state of the safety cap, which is shown in FIGS. 6–8, the syringe or cannula rests in the radial direction merely against the soft, elastic component, whereas the axial support is provided by the rigid component.

Figure 11:
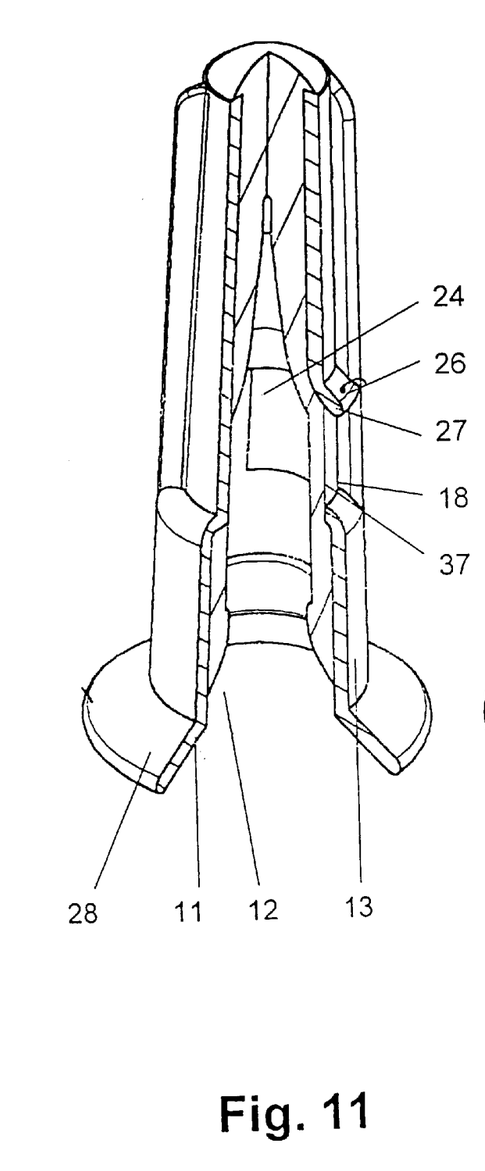
FIG. 11 shows a perspective view of a second exemplary embodiment of a safety cap, which is provided with safety tongues near its lateral openings.
Figure 12:
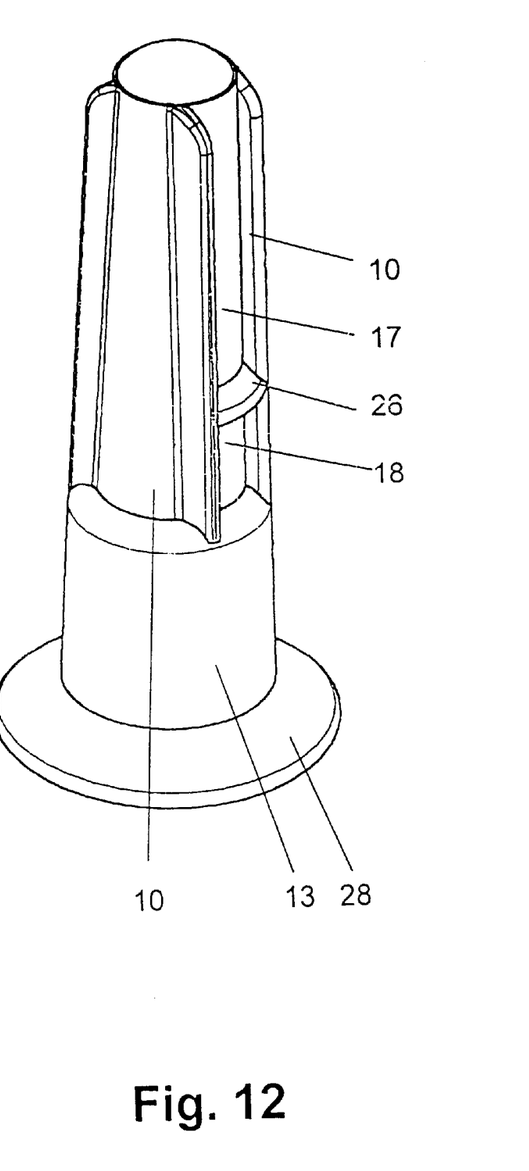
FIG. 12 shows the same view as that of FIG. 11 but in a partially cut-away state.

The second exemplary embodiment, shown in FIGS. 11 and 12, represents a modification of the first exemplary embodiment, so that only the features which are different are explained in the following.

A special feature of the second exemplary embodiment is the design of the edge areas at the top, seen in the insertion direction of the cannula, of the lateral openings 18. This edge area is designed as an outward projecting, protective tongue 26, which, slanting or curving outward toward the insertion opening 12, forms an extension of the wall of the recessed area 17. The axial end of the protective tongue 26, however, remains within the groove formed between the respective ribs 21. The angled surface 27 formed by the protective tongue 26 on the inside prevents the cannula from projecting out of the outer sleeve 10 even if the cannula has assumed an extreme slant and under certain conditions is able to correct the path of the cannula tip, redirecting it to the interior of the safety cap. The addition of the protective tongue 26 makes it possible to increase the area available for placement of the lateral openings 18 or to increase the cross-sectional size of the openings themselves, as will be explained briefly below.

The maximum slant of the cannula is limited in practice by the base of the syringe or by the cone around the cannula, which, if slanted, will eventually strike some part of the safety cap; as a result it is impossible for the cap to be set down at an extreme angle. If a lateral opening 18 is located very close to the insertion opening 12 of the safety cap, it is possible for the cannula to assume a relatively severe slant before the stopping action occurs. The base area 11 of the outer sleeve 10 is therefore not the most suitable place for the lateral openings 18. The maximum possible slant of the cannula decreases as the depth of its insertion increases. By shifting the top edge of the lateral openings 18 even slightly outward, it is possible to achieve a considerable gain in the length of the lateral openings 18 in the longitudinal direction, since the cannula can no longer reach the lateral openings 18. The position of the lateral openings 18 shown in FIG. 12 at the top of the base section 11 and approximately in the middle of the outer sleeve 10 is especially favorable in this regard and can also be considered favorable in terms of the speed with which sterilization can be performed.

Another special feature of the second exemplary embodiment is to be found in the design of the bottom edge of the safety cap, which has a collar 28 extending in the radial direction to help protect the fingers and to improve the reliability with which the cannula can be inserted into the outer sleeve 10. The collar 28 is slightly funnel-shaped or conical, so that, if the person handling the cannula should miss the insertion opening 12, the cannula will not slip off to the side and reach the area where the person's fingers are gripping the cap. The funnel-like shape is able to correct for inaccurate guidance in the direction of the insertion opening 12.

A third exemplary embodiment is shown in FIG. 13, the design of which is similar to that of the first exemplary embodiment. In correspondence with the second exemplary embodiment, however, it is also possible for the safety cap according to FIG. 13 to be provided with protective tongues in the area of the lateral openings 18. The third exemplary embodiment differs from the previously described examples by the presence of transverse ribs 40, which are provided on the gripping surfaces 22 of the top section 14, so that the safety cap to be gripped without slipping. Instead of the ribs, it is possible to provide transverse grooves, nubs, or the like on the outer sleeve 10. In yet another variant, the ribs 40 are formed out of the material of the flexible component, which can either be injected onto the outside or made as a unit with the seal element 30 and allowed to project to the outside through a set of appropriate transverse slots in the outer sleeve 10.

In the following, a fourth exemplary embodiment of a safety cap for a cannula is described on the basis of FIGS. 14–17. This differs from the first exemplary embodiment primarily with respect to the design of the outer sleeve 10 and specifically with respect to the formation and arrangement of the lateral openings 18 and the design of the ribs 21 on the base body 20.

The safety cap of the fourth exemplary embodiment, like the first exemplary embodiment, consists of an outer sleeve 10 of a rigid plastic component and a seal element 30 of a flexible plastic component, held inside the outer sleeve.

Figures 14, 15:
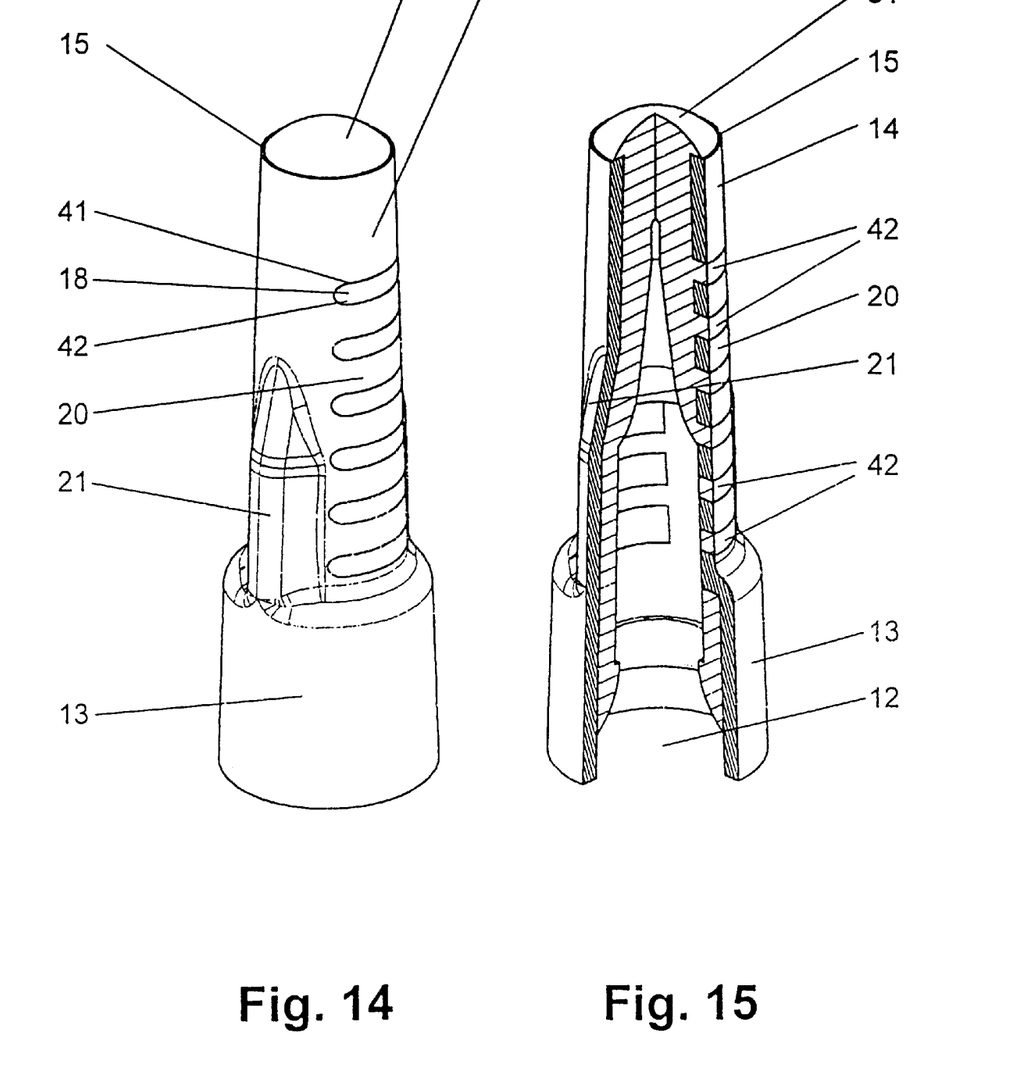
FIG. 14 shows a perspective view of a fourth exemplary embodiment of a safety cap for a cannula.
FIG. 15 shows another perspective view of the fourth exemplary embodiment, in which a quarter-segment of the safety cap has been cut away.
Figure 16:
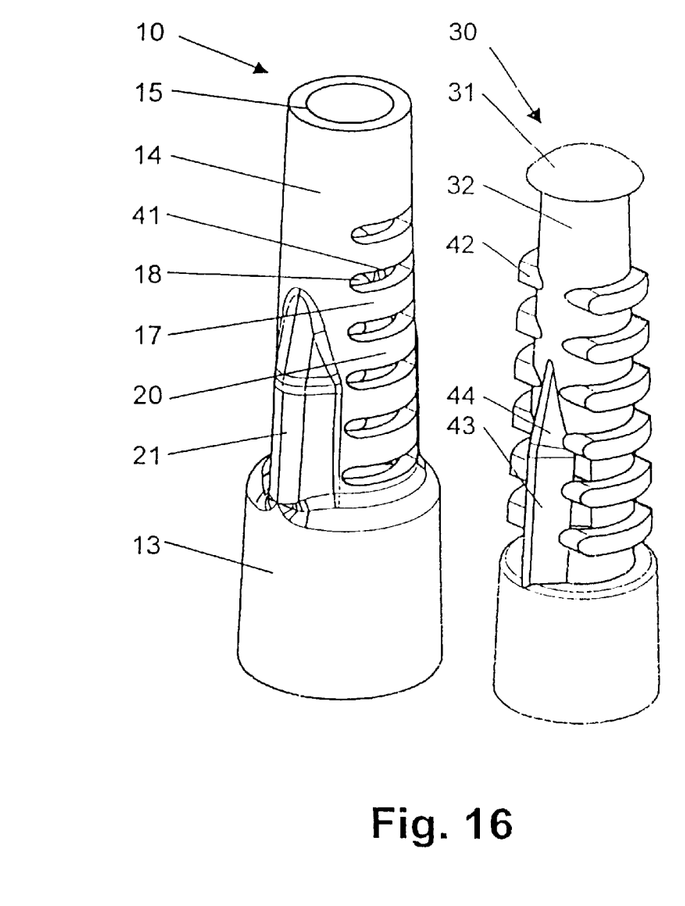
FIG. 16 shows a perspective view of an outer sleeve and a seal element of the safety cap according to the fourth exemplary embodiment, which here are shown next to each other for the sake of illustration.
Figure 17:
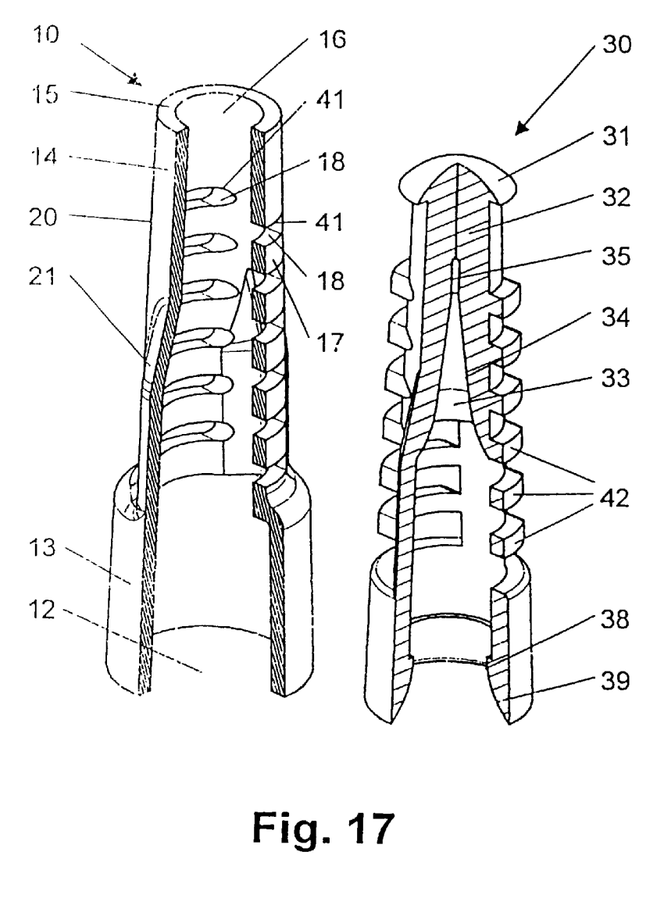
FIG. 17 shows a perspective view corresponding to FIG. 16, but with a partially cut away outer sleeve and a partially cut-away seal element.

As can be seen especially in FIGS. 14, 16, and 17, the outer sleeve 10 has a base section 13, to which a top section 14 is directly connected. The top section 14 comprises a cylindrical base body 20, which tapers conically toward a top end 15; this base body is designed as a sleeve with a pass-through opening 16. The essentially conical external form of the base body 20 is interrupted by two ribs 21, which extend in the longitudinal direction of the safety cap, and which begin immediately at the base section 13. In the illustrated exemplary embodiment, the ribs 21 are arranged opposite each other and terminate approximately in the middle of the top section 14, so that, between two adjacent ribs 21, a recessed section 17, as it were, is formed, in which the lateral openings 18 are provided. The ribs 21, however, extend the greater external width of the base section 13 into the area of the top section 14. The ribs 21 not only improve the options for gripping the cap but also prevent the cap from rolling away after it has been removed from the syringe.

It can be seen from FIG. 14 that several lateral openings 18 are provided between two adjacent ribs 21; these openings are also present beyond the ribs 21 in the longitudinal direction of the safety cap and take the form here of essentially parallel, elongated slots 41, which are transverse to the longitudinal direction of the safety cap. The use of a plurality of slots 41 shortens the penetration routes taken by the sterilization medium. Because of the narrowness of the slots 41 in the longitudinal direction of the safety cap, the tip of a cannula is prevented from penetrating into one of these slots and from projecting out beyond them.

The slots 41 in the outer sleeve 10 are filled by the material of the flexible component, as a result of which complementary, rib-like shoulders are obtained on the seal element 30. In FIG. 15, the rib-like shoulders 42 line up flush with the outside wall of the base body 20. Nevertheless, it is also possible for the shoulders 42 to project slightly beyond the outside wall of the base body 20, as a result of which a grooving is created, which increases the security with which the safety cap can be gripped between the ribs 21. As is especially clear from FIG. 16, the seal element 30 has two rib-like projections 43 with ends 44 which are beveled off toward the top end 15. These beveled ends are located in the area of the ribs 21 of the outer sleeve 10 and engage in corresponding recesses in the inside wall of the outer sleeve 10.

Otherwise, the seal element 30 of the fourth exemplary embodiment is designed in the same way as the seal element 30 of the first exemplary embodiment, this pertaining in particular to the interior shape with the channel 33, closed at one end, for seal off the opening at the tip of the cannula.

Even though a particular embodiment of the invention has been illustrated and described herein, it is not intended to limit the invention and changes and modifications may be made therein within the scope of the following claims.

What is claimed is:

1. Safety cap for a cannula, comprising an outer sleeve (10) having a rolling end (11) and a top end (12) made of a rigid plastic material and a seal element (30) made of a gas-permeable, flexible plastic, said outer sleeve (10) and said seal element (30) being integrally connected with each other so that there is no gap between them, said outer sleeve (10) having an essentially cylindrical base section (13) at its bottom end (11), means defining an insertion opening (12) in said base section for the cannula, a top section (14) connected to said base section (13) and extending all the way to the top end (15) of the outer sleeve (10), and means defining a pass-through opening (16) in said sleeve (10), in which the seal element (30) is located, closing off the top end (15) of the outer sleeve, said outer sleeve (10) being interrupted by at least one lateral opening (18) in its long side between the bottom end (11) and the top end (15), wherein the lateral opening (18) is arranged directly adjacent to the bare section (13) of the outer sleeve (10) and continues into the top section (14), with the lateral opening (18) extending into the region of the seal element (30), in which the channel (33) for reception of the cannula is located, and the lateral opening (18) of the outer sleeve is filled completely by the seal element (30), and of a thickness corresponding to the thickness of the wall of the outer sleeve (10), said insertion opening being of a predetermined diameter and the lateral opening spaced a predetermined axial distance from the lower edges of the base section (13) to limit the angle of the cannula so that it does not pierce the lateral opening (18).

2. Safety cap according to claim 1, wherein the top section (14) has an essentially cylindrical base body (20), which tapers slightly toward the top end (15), which is provided with preferably at least two ribs (21), each of which begins at the base section (13) and extends in the longitudinal direction of the safety cap.

3. Safety cap according to claim 2, wherein the ribs (21) are arranged at a slant to the radial direction of the outer sleeve (10) in such a way that the top section (14) has the shape of an H in cross section.

4. Safety cap according to claim 3, wherein the lateral opening (18) is located in a wall section (17) between the essentially parallel ribs (21).

5. Safety cap according to claim 2, wherein the top section (14) has, in reference to the longitudinal direction of the safety cap, two opposing narrow sides and two opposing wide sides, the latter being designed as gripping surfaces provided with anti-slip holes (41).

6. Safety cap according to claim 2, wherein the top section (14) has, in reference to the longitudinal direction of the safety cap, two opposing narrow sides and two opposing wide sides, the latter being designed as gripping surfaces provided with anti-slip projections (40).

7. Safety cap according to claim 2, wherein the top section (14) has a cylindrical base body (20) with ribs (21) with extending in the longitudinal direction of the safety cap, said base body tapering conically toward the front end (15), whereby the conically tapering base body (20) has between each pair of adjacent ribs (21), several lateral openings (18), which are designed as elongated slots (41) transverse to the longitudinal direction of the safety cap and which are filled completely by the material of the flexible plastic component.

8. Safety cap according to claim 1, wherein the top edge of each opening (18) thus facing the top end (15) of the sleeve, is designed as an outwardly projecting protective tongue (26), having an interior wall surface (27) which slants inward toward the top end (15).

9. Safety cap for a cannula, comprising an outer sleeve (10) having a rolling end (11) and a top end (12) made of a rigid plastic material and a seal element (30) made of a gas-permeable, flexible plastic, said outer sleeve (10) and said seal element (30) being integrally connected with each other so that there is no gap between them, said outer sleeve (10) having an essentially cylindrical base section (13) at its bottom end (11), means defining an insertion opening (12) in said base section for the cannula, a top section (14) connected to said base section (13) and extending all the way to the top end (15) of the outer sleeve (10), and means defining a pass-through opening (16) in said sleeve (10), in which the seal element (30) is located, closing off the top end (15) of the outer sleeve, said outer sleeve (10) being interrupted by at least one lateral opening (18) in its long side between the bottom end (11) and the top end (15), wherein the lateral opening (18) is arranged directly adjacent to the base section (13) of the outer sleeve (10) and continues into the top section (14), with the lateral opening (18) extending into the region of the seal element (30), in which the channel (33) for reception of the cannula is located , and the lateral opening (18) of the outer sleeve is filled completely by the seal element (30), and of a thickness corresponding to the thickness of the wall of the outer sleeve (10), said insertion opening being of a predetermined diameter and the lateral opening spaced a predetermined axial distance from the lower edges of the base section (13) to limit the angle of the cannula so that it does not pierce the lateral opening (18).

10. Safety cap for a cannula, comprising an outer sleeve (10) having a rolling end (11) and a top end (12) made of a rigid plastic material and a seal element (30) made of a gas-permeable, flexible plastic, wherein said outer sleeve (10) and said seal element (30) are formed jointly by a two-component injection molding method and are integrally connected with each other so that there is no gap between them, said outer sleeve (10) has an essentially cylindrical base section (13) at its bottom end (11), means defining an insertion opening (12) in said base section for the cannula, a top section (14) connected to said base section (13) and extending all the way to the top end (15) of the outer sleeve (10), and means defining a pass-through opening (16) in said sleeve (10), in which the seal element (30) is located, closing off the top end (15) of the outer sleeve, said outer sleeve (10) being interrupted by at least one lateral opening (18) in its long side between the bottom end (11) and the top end (15), wherein the lateral opening (18) is arranged directly adjacent to the base section (13) of the outer sleeve (10) and continues into the top section (14), with the lateral opening (18) extending into the region of the seat element (30), in which the channel (33) for reception of the cannula is located, and the lateral opening (18) of the outer sleeve is filled completely by the seal element (30), with a thickness corresponding to the thickness of the wall of the outer sleeve (10).

* * * * *